United States Patent [19]

Arnaud et al.

[11] Patent Number: 4,677,379
[45] Date of Patent: Jun. 30, 1987

[54] PROCESS AND DEVICE FOR THE DETECTION OF CRACKS IN RIVETED JOINTS USING AN EDDY CURRENT PROBE

[75] Inventors: Jean-Louis Arnaud, Verrieres-le-Buisson; Michel Floret, Gennevelliers, both of France

[73] Assignee: Societe Nationale Industrielle et Aerospatiale, France

[21] Appl. No.: 574,171

[22] Filed: Jan. 26, 1984

[30] Foreign Application Priority Data

Feb. 24, 1983 [FR] France ................................. 83 03043

[51] Int. Cl.[4] ...................... G01N 27/82; G01R 33/12
[52] U.S. Cl. ..................................... 324/242; 324/240
[58] Field of Search ................. 324/225, 227, 239–243

[56] References Cited

U.S. PATENT DOCUMENTS

| 3,852,820 | 7/1974 | Flaherty et al. | 324/227 |
| 3,956,618 | 5/1976 | Götz | 324/207 |
| 4,107,605 | 8/1978 | Hudgell | 324/227 |
| 4,194,149 | 3/1980 | Holt et al. | 324/225 |

Primary Examiner—Reinhard J. Eisenzopf
Assistant Examiner—Walter E. Snow
Attorney, Agent, or Firm—Fisher, Christen & Sabol

[57] ABSTRACT

The present invention relates to a process and device for the non-destructive examination of riveted joints or the like, particularly for monitoring the fuselage of an aircraft. According to the invention, an eddy current probe is used and two rectangular components of the signal of unbalance from the latter are compared with thresholds predetermined by prior measurements on similar new joints, in order to determine the presence and/or the absence of cracks.

5 Claims, 11 Drawing Figures

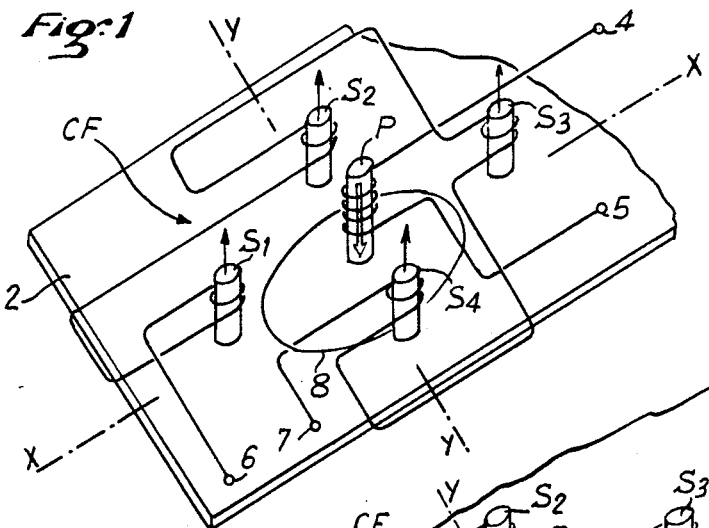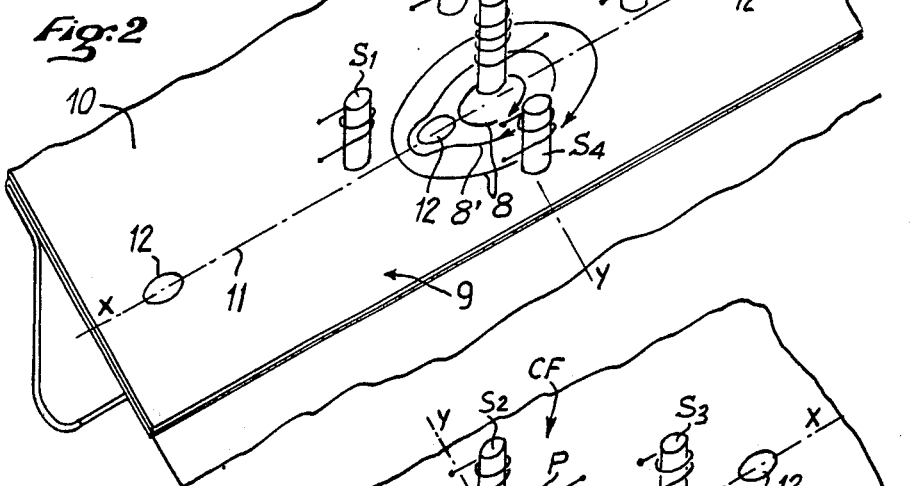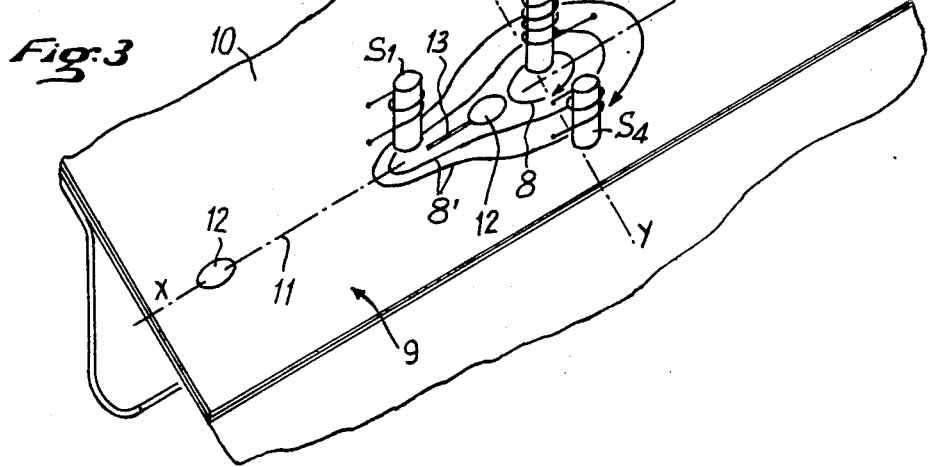

PROCESS AND DEVICE FOR THE DETECTION OF CRACKS IN RIVETED JOINTS USING AN EDDY CURRENT PROBE

The present invention relates to a process and a device for the non-destructive examination of riveted joints or the like by means of a probe employing eddy currents. Although the invention may be carried out in numerous applications, it will be described hereinafter more particularly in connection with the non-destructive examination of the joints of the panels constituting the skin of the fuselage of an aircraft.

The skin of the fuselage of an aircraft is known to be constituted by individual panels assembled together by riveted joints in which said rivets are aligned and equidistant. Such riveted joints are subject to considerable fatigue in the course of use of the aircraft, particularly by reason of the cycles of compression and decompression to which the fuselage thereof is subjected. This may result in the formation of cracks which develop from the holes through which the rivets pass in the panels. Consequently, the joints weaken and it is therefore indispensable to monitor said joints periodically in order to know the state thereof.

Non-destructive examination of the riveted joints of the skin of an aircraft is generally carried out by means of an ultra-sound probe. However, the use of such a probe is long and fastidious, particularly as a correct coupling must be effected between the probe and the rivet examined (for example with the aid of vaseline) and by reason of the precision required for positioning the probe with respect to the rivet. From these points of view, it would be interesting to be able to use a probe employing eddy currents; however, the signals delivered by such a probe are not easy to exploit. In fact, if an eddy current probe, correctly balanced and oriented, is made to advance along a line of sound rivets, i.e. of which the holes for passage in the panels are not cracked, a signal is obtained whose cycle is flat and elongated.

On the other hand, if said probe encounters a rivet associated with a crack, it furnishes a wide crossed loop cycle. In either case, it is impossible for an observer to make the points of the cycle correspond to the positions of the probe along the line of the rivets.

It is an object of the present invention to enable such an eddy current probe to be used in an apparatus for non-destructive examination of automatic or at least semi-automatic type for monitoring riveted joints or the like.

To this end, according to the invention, the process for the non-destructive examination of riveted joints or the like by means of a probe employing eddy currents, said joints comprising a succession of aligned and equidistant rivets or the like, is noteworthy in that an eddy current probe is used which is capable of furnishing, when it is advanced along said succession of rivets, a signal in a cycle which, related to a system of orthogonal axes X—X and Y—Y of which one, X—X, is parallel to the displacement of said probe, is flat and elongated along said axis X—X, when the rivet in the course of examination is not associated with a crack, but, on the contrary, is constituted by a wide crossed loop extending both parallel to axis X—X and parallel to axis Y—Y when the rivet in the course of examination is associated with a crack, and in that the following operations are successively carried out:

a large quantity of control joints similar to the one which is to be examined in non-destructive manner is firstly examined with the aid of said probe, said control joints being sure not to comprise cracks, and the plurality of corresponding flat and elongated cycles is recorded;

from the envelope of this plurality of flat and elongated cycles is determined, along axis X—X, a first threshold $S_{Ro}$ beyond which it is sure that the signal from the probe indicates the presence of a rivet and, along axis Y—Y, a second threshold $S_{co}$ beyond which it is sure that the signal from the probe indicates the presence of a crack;

after which said probe is advanced along the succession of rivets to be examined and the components of the signal from the probe along axes X—X and Y—Y are continuously measured;

said components of the signal from the probe are then compared respectively with thresholds $S_{Ro}$ and $S_{co}$, in order to deduce therefrom the presence or absence of cracks; and the results of the comparison are recorded and/or displayed.

Thanks to the invention, simple criteria for determining the presence or the absence of cracks are thus obtained. The object of the preliminary phase of recording is to take into account the possible variations of the characteristics of the joints due to the manufacturing tolerances, the variations in positioning of the probe, the variations in the materials constituting the panels of skin and the rivets, etc. . . . and it may be carried out on the joints of new aircraft whose model is identical to those whose joints are to be subsequently inspected. It will be noted that the simultaneous comparison of the components of the signal from the probe with the two thresholds $S_{Ro}$ and $S_{co}$ establishes the coincidence of the presence of a rivet and of a possible crack, in certain manner.

For carrying out the process according to the invention, a device for the non-destructive examination of riveted joints or the like comprises a probe employing eddy currents capable of furnishing, when it is advanced along a succcession of aligned and equidistant rivets or the like, a signal in a cycle which, related to a system of orthogonal axes X—X and Y—Y of which one, X—X, is parallel to the displacement of said probe, is flat and elongated along said axis X—X, when the rivet being examined is not associated with a crack, but, on the contrary, is constituted by a wide crossed loop extending both parallel to axis X—X and parallel to axis Y—Y when the rivet being examined is associated with a crack; memory means for storing said thresholds $S_{Ro}$ and $S_{co}$; means for controlling and reading said probe for continuously measuring the components of the signal from the probe along axis X—X and Y—Y; means for comparing said components with said thresholds $S_{Ro}$ and $S_{co}$; and means for recording and/or displaying the results of the comparison.

Said eddy current probe preferably comprises a central primary injection winding surrounded by four peripheral secondary detection windings, said secondary windings being angularly distributed equally on the same circle centred on the primary winding and disposed in two's along two right-angled diameters, one of said diameters being adapted to merge with said aligned succession of rivets, two diametrically opposite secondary windings being of the same direction, but of direction opposite the other two secondary windings and the four secondary windings being connected in series so that two consecutive windings are of opposite directions.

The distance separating the primary injection winding from a secondary detection winding is equal to half the distance separating two consecutive rivets in said succession of rivets.

In order to compensate the phase shift undergone by the detection signal from the probe in said control and reading means, the latter advantageously comprise a controllable phase shift device. The two components of the signal from the probe along the axes X—X and Y—Y are obtained in conventional manner by a double synchronous demodulator in quadrature.

In an advantageous embodiment, the memory means for storing the thresholds $S_{Ro}$ and $S_{co}$ and the means for comparing said components of the signal from the probe with the thresholds $S_{Ro}$ and $S_{co}$ are formed by a microprocessor.

The invention will be more readily understood on reading the following description with reference to the accompanying drawings, in which:

FIG. 1 is a schematic view in perspective of the probe employing eddy currents according to the present invention.

FIGS. 2 and 3 respectively illustrate the influence of a sound rivet and of a rivet associated with a crack on the lines of current generated by the probe of FIG. 1.

FIG. 4 gives the block diagram of the device for controlling and reading the probe of FIG. 1.

Figure 11:
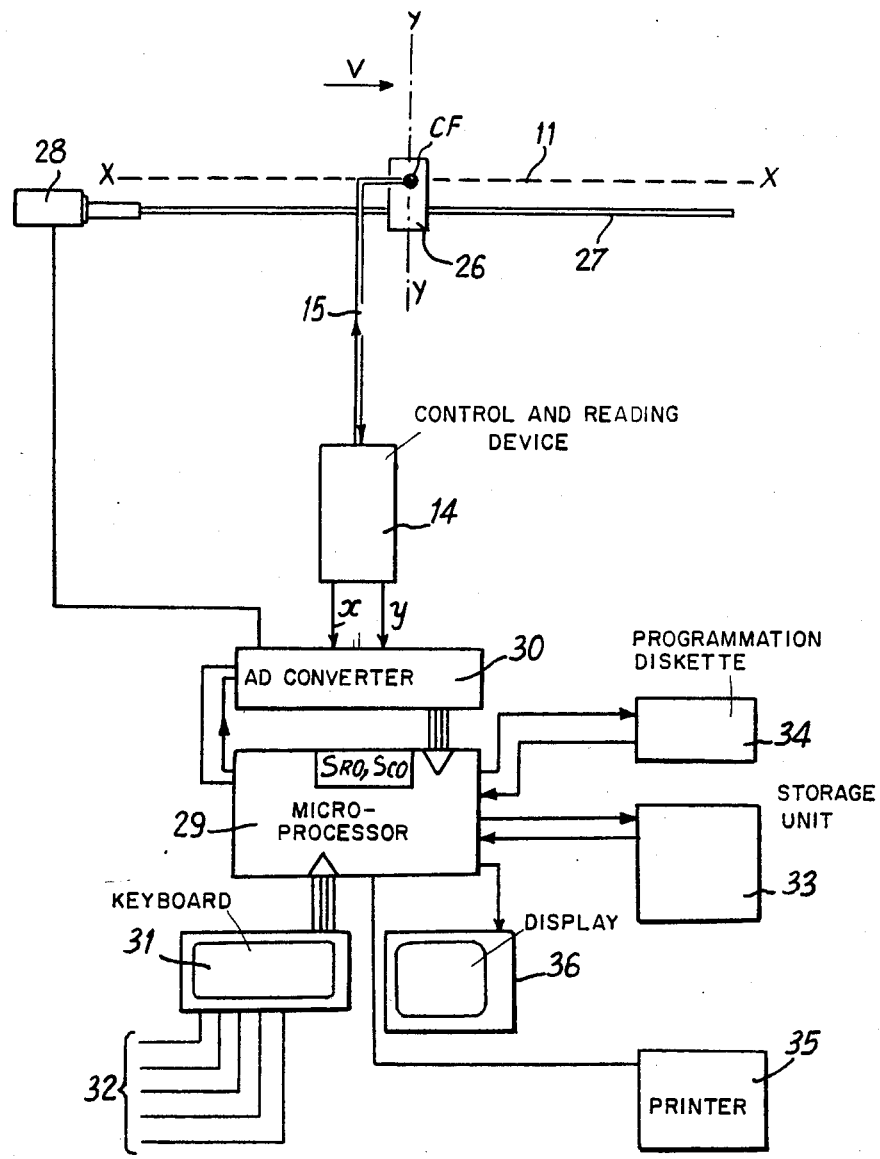

FIG. 11 gives the synoptic diagram of the device for non-destructive examination employing eddy currents, in accordance with the invention.

In these Figures, like references designate like elements.

Figure 5:
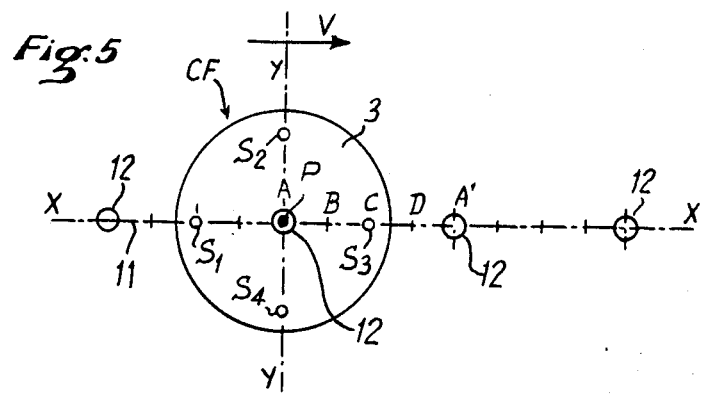
FIGS. 5 to 7 illustrate the functioning of the probe of FIG. 1 and of the device of FIG. 4, when said probe is displaced along a line of rivets not associated with cracks.
Figure 8:
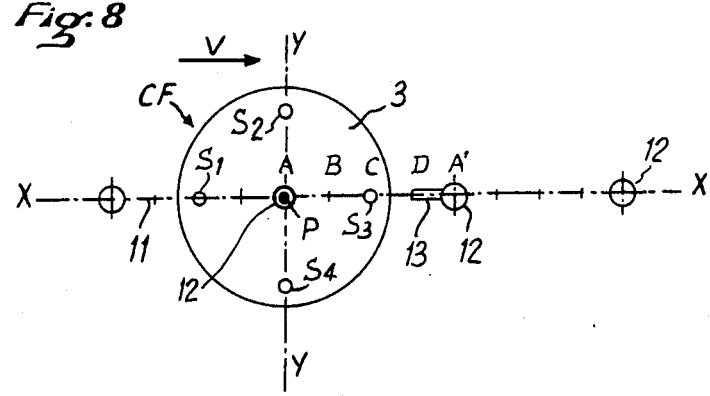
FIGS. 8 to 10 illustrate the functioning of the probe of FIG. 1 and of the device of FIG. 4, when said probe encounters a rivet associated with a crack.

Referring now to the drawings, the eddy current probe CF which is shown schematically in perspective in FIG. 1 above a surface 2 to be examined, comprises a primary injection winding P and four secondary detection windings $S_1$ to $S_4$, each of the primary and secondary windings comprising a ferrite core or the like and these five windings and their cores being embedded in a body 3 of magnetically and electrically insulating material (not shown in FIGS. 1 to 3 but visible in FIGS. 5 and 8). In this body 3, the relative positions of the five windings are set, the injection winding P being disposed centrally, whilst the detection windings $S_1$ to $S_4$ are diametrically opposite in two's, the windings $S_1$ and $S_3$ determining an axis X—X at right angles to an axis Y—Y determined by the windings $S_2$ and $S_4$. The axis of the injection winding P passes through the point of intersection of axes X—X and Y—Y and the windings $S_1$ to $S_4$ are equidistant from this point of intersection.

The injection winding P is provided with two terminals 4 and 5 between which an electric excitation signal is injected, whilst windings $S_1$ to $S_4$ are mounted in series so that detection windings $S_1$ and $S_3$ are in the same direction and windings $S_2$ and $S_4$ are in opposite direction to windings $S_1$ and $S_3$. The series assembly of detection windings $S_1$ to $S_4$ comprises two terminals 6 and 7 between which the detection signal, i.e. a signal of unbalance from the probe, is collected.

Windings $S_1$ to $S_4$ are identical and balanced so that, when the injection winding P receives the injection signal between its terminals 4 and 5, it generates in a homogeneous surface 2 currents induced along circular lines of currents 8 and producing in the detection windings $S_1$ to $S_4$ signals which are equal and opposite in two's, so that the signal at terminals 6 and 7 is zero. In the arrangement of FIG. 1, windings $S_1$ and $S_3$ are considered as windings of meaurement, whilst windings $S_2$ and $S_4$ are considered as windings of compensation.

When the surface above which the probe CF lies is not homogeneous, the lines of currents induced by the injection winding P are no longer circular and undergo deformations in the vicinity of the heterogeneities. FIG. 2 illustrates a heterogeneous surface 9, for example the skin of an aircraft fuselage constituted by individual panels 10 of aluminium assembled by lines 11 of titanium rivets 12, and the probe CF has been disposed so that its axis X—X is superposed on an axial line 11 of rivets 12. This FIG. 2 shows that the lines of induced currents 8 remote from a rivet 12 remain circular and that the lines of induced currents 8' close to a rivet undergo deformations surrounding said rivet. In FIG. 3, similar to FIG. 2, it has been further assumed that an individual panel 10 comprised a crack 13, having for origin the hole through which a rivet 12 passes, and this Figure shows that the deformations of the lines of induced currents are even more accentuated.

In this way, a probe CF balanced to give a zero signal between its output terminals 6 and 7 when the surface 2 is homogeneous or when it is located opposite a homogeneous part of a heterogeneous surface 9, will furnish a signal of unbalance when the lines of induced currents undergo deformations due to heterogeneities 12 or 13.

Figure 4:
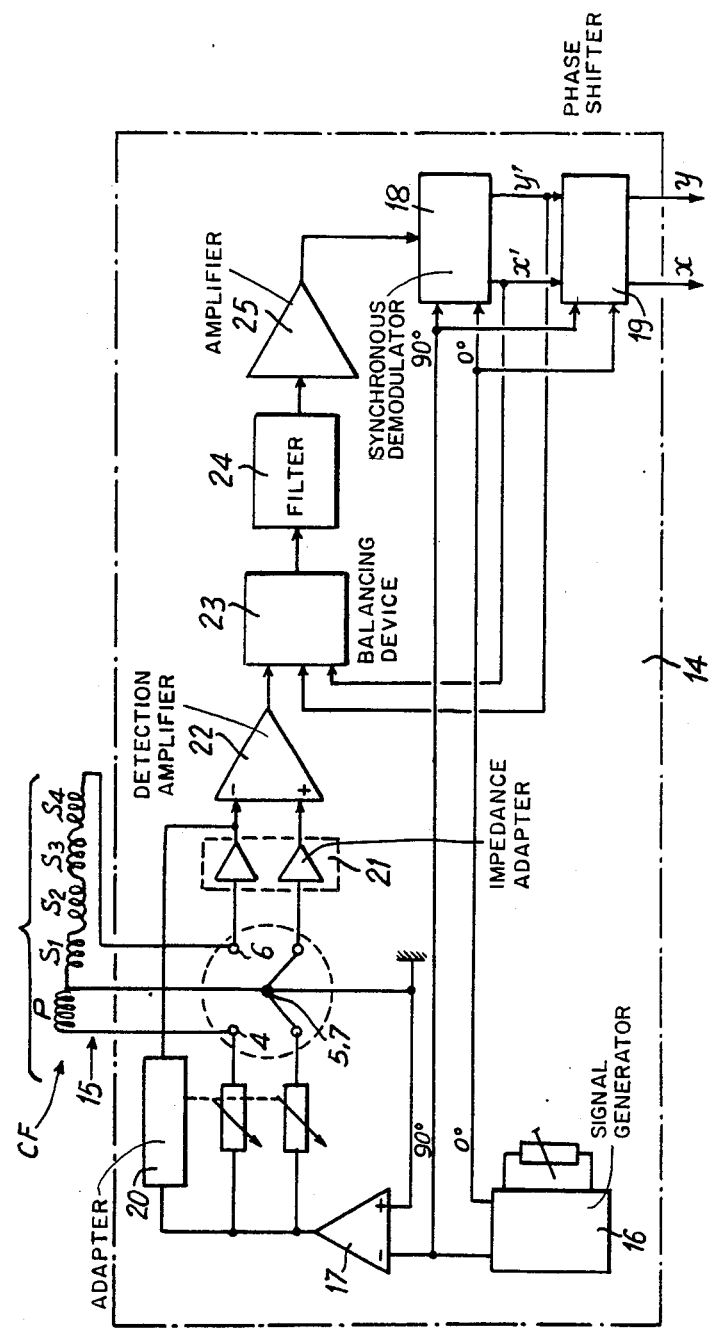

As shown in FIG. 4, the probe CF is mounted in a control and reading device 14, via a link 15. The device 14 comprises an electric generator 16 of a signal at carrier frequency, preferably sinusoidal, and of a signal at the same frequency but phase shifted rearwardly through 90°. A reference signal of phase 90° intended for serving as injection signal and a reference signal of phase 0° are thus obtained. The injection signal (phase 90°) is applied, on the one hand, to a current adapter amplifier 17 and, on the other hand, to a double synchronous demodulator 18 and to a phase shifter 19. The reference signal of phase 0° is applied to the double synchronous demodulator 18 and to the phase shifter 19.

At the output of the amplifier 17, the injection signal is transmitted to the primary winding P via an adaptation detector 20.

Furthermore, the secondary windings $S_1$ to $S_4$ are connected to an impedance adapter system 21 followed by a detection amplifier 22, a device 23 for balancing the probe CF, a possible filter 24 adapted to eliminate the parasitic frequencies from the carrier frequency and an amplifier 25. In this way, the injection signal applied by the generator 16 to the primary winding P via the amplifier 17 and the adapter 20 is detected by the windings $S_1$ to $S_4$, then adapted in impedance in the adapter 21, after which, after amplification (in 22), balancing (in 23), filtering (in 24) and amplification (in 25), it is applied to the double demodulator 18. The latter demodulates the carrier wave by extracting the two components x' and y' in quadrature from the possible signal of unbalance which is due to a heterogeneity 12 or 13.

Finally, the two orthogonal components x' and y' of the signal of unbalance, which have undergone a phase shift in the portion of circuit $S_1$ to $S_4$, 21 to 25, are addressed to the phase shifter 19, which delivers at its output two components x and y in phase with the axes X—X and Y—Y, respectively.

In FIG. 5, it has been assumed that the probe CF was moving in the direciton of arrow V, so that its axis X—X remains constantly merged with the axial line 11 of the rivets 12, that the distance separating the centre of the primary injection winding P from the centre of each of the secondary detection windings $S_1$ to $S_4$ was equal to half the distance separating the centres of two consecutive rivets 12, and that no crack 13 existed.

If, in the initial position, the axis of the primary injection winding P passes through the centre A of a rivet 12, each of windings $S_1$ to $S_4$ is sufficiently remote from a rivet 12 for the portion of surface embraced by the probe CF to appear homogeneous to said probe. Therefore, no signal of unbalance appears between the terminals 6 and 7, if the balance of the probe CF effected by the device 23 is correct. In a system of right-angled axes X—X, Y—Y (cf. FIG. 7) identical to the corresponding axes of the probe CF, the signal of unbalance is then shown by the origin O of said axes. It will be noted that, further to the phase shift $\theta$ mentioned above and corrected by the phase shifter 19, at the output of the double synchronous demoulator 18 in quadrature, the system of right-angled axes X—X, Y—Y has undergone a rotation of amplitude $\theta$, axes X—X and Y—Y occupying the positions X'—X' and Y'—Y' respectively.

When the probe CF is displaced towards the right in FIG. 5 in the direction of rivet 12 with centre A', the characteristic point of the signal of unbalance between the terminals 6 and 7 describes a portion of curve $K_1$ (cf. FIGS. 6 and 7) which, starting from the origin O of the axes, moves away from axis X—X or X'—X' and joins the latter at Q, when the axis of winding P reaches point B of line 11, located at a quarter of the distance between the two adjacent rivets 12. If the probe CF continues its movement of advance, the characteristic point of said signal of unbalance describes a portion of curve $K_2$ (opposite portion $K_1$ with respect to axis X—X or X'—X') moving closer to axis Y—Y or Y'—Y'. This portion of curve $K_2$ stops at R, when the axis of winding P reaches point C, centre of the distance separating the two adjacent rivets 12.

When said axis of the winding P passes from point C to point D (corresponding to three quarters of the distance between two adjacent rivets 12), said characteristic point describes, in opposite direction, the portion of curve $K_2$ from point R to point Q. Finally, when the axis of winding P passes from point D to point A', said characteristic point describes the portion of curve $K_1$ from Q towards O.

In this way, if probe CF is displaced along a line 11 comprising a plurality of identical, regularly spaced apart rivets 12, the characteristic point of the signal of unbalance between terminals 6 and 7 describes, cyclically and successively, the portion of curve $K_1$ from O towards Q, then the portion of curve $K_2$ from Q towards R, then the portion of curve $K_2$ from R towards Q, then the portion of curve $K_1$ from Q towards O, then the portion of curve $K_1$ from O towards Q, etc. . . . However, due to the possible variations in positioning of the probe, in the materials constituting the rivets 12 and the panels 10, in the distances between rivets, etc. . . . , there is a certain dispersion and the portions $K_1$ and $K_2$ are not necessarily absolutely identical and superposed for all the cycles.

According to the invention, a large number of lines 11 of rivets 12, manufactured in identical manner, are thus examined to know the overall envelope K of the portions of curves $K_1$ and $K_2$. Moreover, a magnitude $X_o$ equal to a fraction, for example, one third, of the length Lo of the envelope K, as well as the height $Y_o$ thereof with respect to axis X—X, are measured. This magnitude $X_o$ is intended to determine a threshold $S_{Ro}$ beyond which it is sure that the signal of unbalance appearing between terminals 6 and 7 corresponds to the presence of a rivet. Furthermore, the height $Y_o$ makes it possible to determine a threshold $S_{co}$ beyond which it is sure that a characteristic point cannot belong to a curve $K_1$, $K_2$ representative of a sound rivet.

Figure 6:
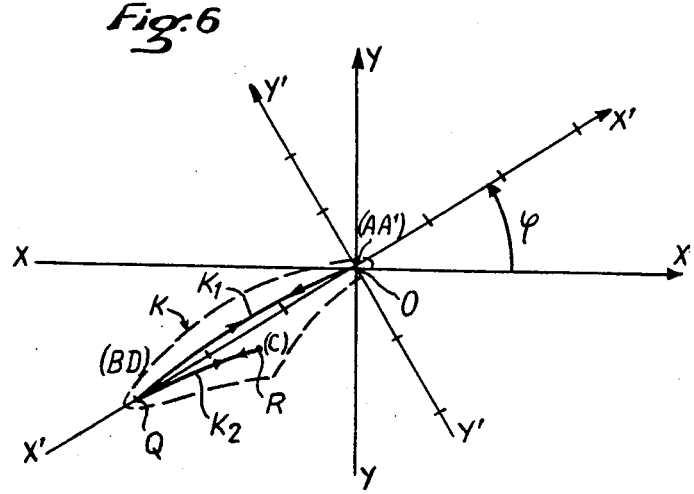
Figure 7:
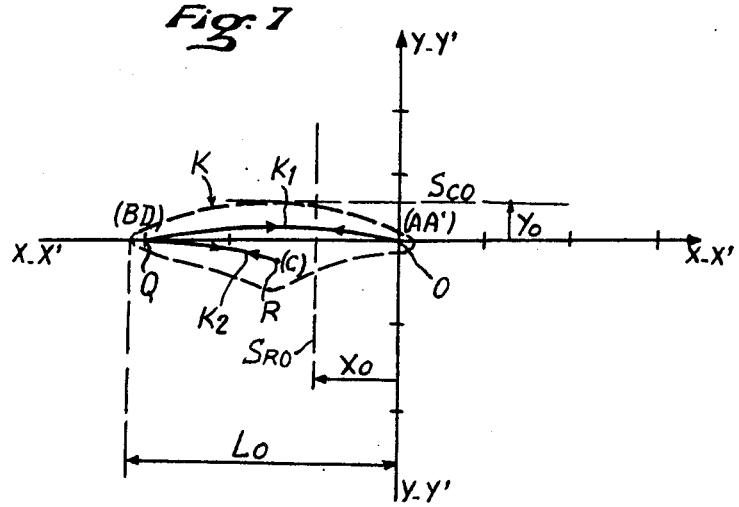
Figure 9:
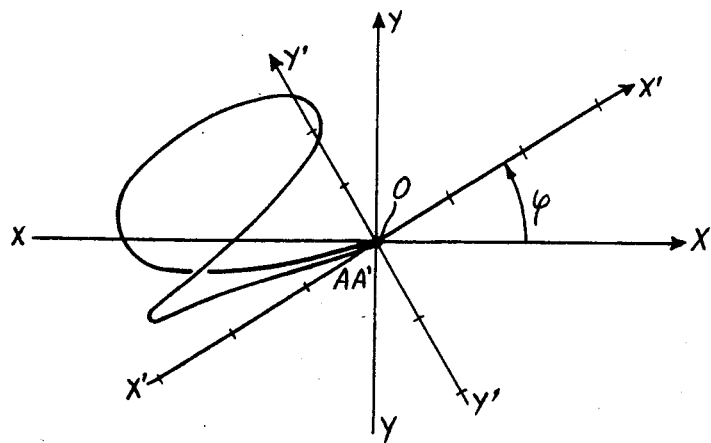
Figure 10:
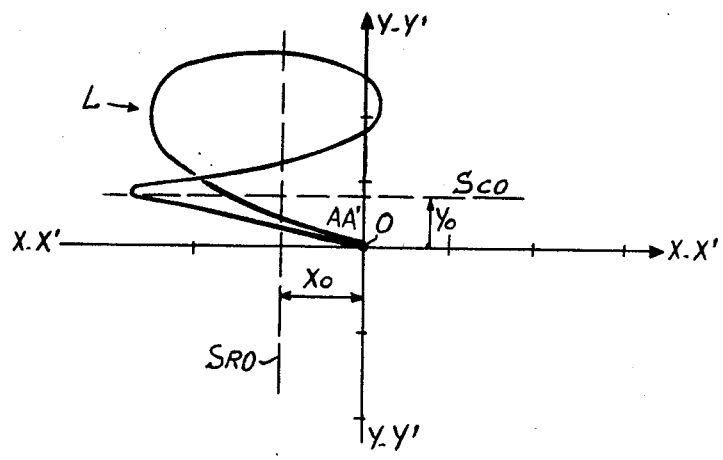

FIGS. 8 to 10 correspond respectively to FIGS. 5 to 7 and illustrate the process of detection when a crack 13 has developed in a panel 10 from the hole through which a rivet 12 passes. It is seen that the curve L described by the characteristic point is very different from curve $K_1$, $K_2$ associated with a sound rivet and largely exceeds the threshold $S_{co}$ parallel to axis Y—Y or Y'—Y', as well as the threshold $S_{Ro}$ parallel to axis X—X or X'—X'.

Thus the fact of exceeding the threshold $S_{Ro}$ means the presence of a rivet 12, whether the latter is sound or cracked, whilst the fact of exceeding threshold $S_{co}$ means a crack 13. Furthermore, analysis of the direction of rotation of the crossed loop shown in FIG. 10 makes it possible to determine the direction of the crack 13 exactly.

According to the invention, the two thresholds $S_{Ro}$ and $S_{co}$ are used for the non-destructive examination of a riveted joint. To this end, the device of which the block diagram has been shown in FIG. 11 may for example be used.

The probe CF is mounted in a probe-holder 26 adapted to slide along a guide rod 27, parallel to line 11 of rivets to be examined, so that the axis X—X of said probe CF merges constantly with said axial line 11. The guide rod 27 is associated with measuring means 28, for example potentiometric or of the type described in U.S. Pat. No. 3,898,555, capable of delivering at each instant the abscissa of the probe CF along the rod 27. The probe CF is controlled and read by device 14 to which it is connected by link 15 (cf. also FIG. 4). The device of FIG. 11 further comprises a microprocessor 29 to which are transmitted, via an analog-to-digital converter 30, the abscissa of the probe CF delivered by the device 28 and the components x and y of the signal of unbalance of said probe. The microprocessor 29 is connected to a keyboard 31 for communicating thereto data 32 such as the identification of the line 11 to be examined, to a storage unit 33, for example of the hard disc type, to a programmation diskette 34, to a printer 35 and to a display device 36.

In a first step of the process according to the invention, the probe CF is advanced in front of a long length and/or a large number of lines 11 bereft of cracks (joints of new aircraft) so that the microprocessor 29 can determine the thresholds $S_{Ro}$ and $S_{co}$ which it memorizes. When the probe CF examines a line 11 of rivets 12 serving to join panels 10 in an aircraft to be monitored, the microprocesor 29 then compares at each instant the components x and y of the signal of unbalance with the thresholds $S_{Ro}$ and $S_{co}$ and it can thus not only detect and count the rivets 12, but can also detect the cracks 13. It furnishes these data to the peripheral apparatus 33, 35 and 36.

What is claimed is:

1. A device for the non-destructive examination of a succession of riveted joints aligned along an X—X axis and orthogonal to a Y—Y axis and spaced equidistantly apart, comprising:

an eddy current probe comprising a central primary injection winding surrounded by four peripheral secondary detection windings, said secondary windings being angularly distributed equally on the same circle centered on the primary winding and disposed in two's along two right-angled diameters (X—X and Y—Y), one of the said diameters (X—X) being adapted to merge with said aligned succession of riveted joints, two diametrically opposite said secondary windings being of the same direction, but of direction opposite the other two said secondary windings and the four said windings being connected in series so that two consecutive windings are of opposite direction;

means for advancing said probe along said X—X axis;

said probe being linked with means for controlling and reading said probe, said means for controlling and reading said probe and said probe generating a cyclic signal when said probe is advanced along said succession of aligned riveted joints, said cyclic signal having a first shape that extends parallel to said X—X axis when one of said riveted joints being examined does not include a crack, and a second shape that extends both parallel to said X—X axis and parallel to said Y—Y axis when one of said riveted joints being examined includes a crack, said controlling and reading means for said probe generating an X component of said cyclic signal in phase with said X—X axis and a Y component of said cyclic signal in phase with said Y—Y axis as said probe is moved along said X—X axis in a direction orthogonal to said Y—Y axis;

memory means for storing a first threshold and a second threshold, said first threshold being measured along said X—X axis such that when said X component is in excess of said first threshold, the presence of at least a riveted joint is detected, and said second threshold being measured along said Y—Y axis such that when said Y component is not in excess of said second threshold the presence of a riveted joint that does not include a crack is detected;

said means for controlling and reading said probe further continuously measuring said components of said cyclic signal;

means for comparing said components with said first and said second threshold having a comparison output; and means for recording said comparison output.

2. The device as claimed in claim 1, wherein the distance separting said primary injection winding from any of said secondary detection windings is equal to half a distance separating two consecutive riveted joints in said aligned succession of riveted joints.

3. The device as claimed in claim 1, further comprising means for displaying said comparison output.

4. A process for the non-destructive examination of a succession of riveted joints aligned along an X—X axis and othogonal to a Y—Y axis and spaced equidistantly apart, comprising:

using an eddy current probe comprising a central primary injection winding surrounded by four peripheral secondary detection windings, said secondary windings being angularly distributed equally on the same circle centered on the primary winding and disposed in two's along two right-angled diameters (X—X and Y—Y), one of said diameters (X—X) being adapted to merge with said aligned succession of riveted joints, two diametrically opposite said secondary windings being of the same direction, but of direction opposite the other two said secondary windings and the four said windings being connected in series so that two consecutive windings are of opposite direction;

advancing said probe along said succession of riveted joints;

linking said probe with means for controlling and reading said probe;

generating a cyclic signal with said probe and said means for controlling and reading said probe during said advancing of said probe, said cyclic signal having a first shape that extends substantially parallel to said X—X axis when one of said riveted joints being examined does not include a crack, and a second shape that extends both parallel to said X—X axis and parallel to said Y—Y axis when one of said joints being examined includes a crack;

generating an X component of said cyclic signal in phase with said X—X axis and a Y component of said cyclic signal in phase with said Y—Y axis during said advancing of said probe along said X—X axis in a direction orthogonal to said Y—Y axis;

recording a plurality of signals having said first shape by examining with said probe a large quantity of control riveted joints similar to said succession of aligned riveted joints being examined, said control joints not including any cracks;

generating an envelope of signals from said plurality of signals having said first shape and determining a first threshold measured along said X—X axis such that when said X component of said cyclic signal is in excess of said first threshold, the presence of at least a riveted joint is indicated;

determining a second threshold measured along said Y—Y axis such that when said Y component of said cyclic signal is not in excess of said second threshold the presence of a riveted joint that does not include a crack is indicated;

thereafter advancing said probe along said succession of aligned riveted joints to be examined and continuously measuring the components of said cyclic signal;

comparing said cyclic signal components with said first and said second thresholds, in order to indicate the presence of riveted joints that do not include any cracks; and recording the results of said comparing said components of said cyclic signal with said thresholds.

5. The process according to claim 4 further comprising the step of displaying the results of said comparing said components of said cyclic signal with said thresholds.

* * * * *